United States Patent [19]

Biere et al.

[11] Patent Number: 4,960,777

[45] Date of Patent: Oct. 2, 1990

[54] HETEROARYLOXY-β-CARBOLINE DERIVATIVES, THEIR PREPARATION AND THEIR USE AS MEDICINAL AGENTS

[75] Inventors: Helmut Biere; Andreas Huth; Dieter Rahtz; Ralph Schmiechen; Dieter Seidelmann; David Stephens, all of Berlin, Fed. Rep. of Germany; Mogens Engelstoft, Vaerlose; John B. Hansen, Lyngby, both of Denmark

[73] Assignee: Schering Aktiengesellschaft, Berlin and Bergkamen, Fed. Rep. of Germany

[21] Appl. No.: 409,899

[22] Filed: Sep. 20, 1989

Related U.S. Application Data

[62] Division of Ser. No. 23,752 Mar. 9, 1987, Pat. No. 4,877,792.

[30] Foreign Application Priority Data

Mar. 8, 1986 [DE] Fed. Rep. of Germany ....... 3608089

[51] Int. Cl.$^5$ .................... A61K 31/38; A61K 31/40; A61K 31/435; C07D 413/12
[52] U.S. Cl. ...................................... 514/253; 514/60; 514/228.2; 514/232.8; 514/255; 514/269; 514/272; 514/274; 544/60; 544/114; 544/121; 544/123; 544/238; 544/295; 544/316; 544/317; 544/318; 544/319; 544/320; 544/357; 544/405
[58] Field of Search .................. 514/228.2, 232.8, 253, 514/255, 272, 274, 269, 58.1, 58.6; 544/238, 316, 317, 318, 319, 320, 405, 295, 123, 121, 114, 357

[56] References Cited

U.S. PATENT DOCUMENTS 4,719,210 1/1988 Seidelman et al. .................. 546/86

4,877,792 10/1989 Riere et al. ............................ 546/86

Primary Examiner—Mary C. Lee
Assistant Examiner—J. Richter
Attorney, Agent, or Firm—Millan, White & Zelano

[57] ABSTRACT

Heteroaryloxy-β-carboline derivatives of general Formula I

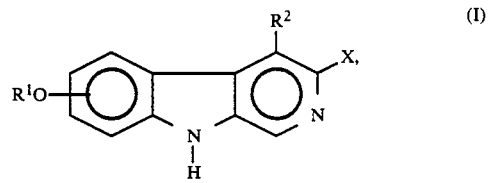

wherein
$R^1$ is an optionally substituted heteroaryl residue,
$R^2$ is hydrogen, lower alkyl or lower alkoxyalkyl,
X is a $COOR^3$-group wherein $R^3$ means H or lower alkyl, or represents a $CONR^4R^5$-group wherein $R^4$ and $R^5$ mean respectively hydrogen or lower alkyl, $R^4$ and $R^5$ being capable of forming, together with the nitrogen atom, a 5- to 6-membered heterocycle, or means an oxadiazolyl residue of the formula

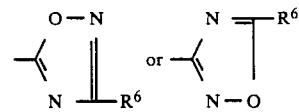

wherein $R^6$ means hydrogen, lower alkyl or cycloalkyl,
are valuable pharmaceuticals.

17 Claims, No Drawings

HETEROARYLOXY-β-CARBOLINE DERIVATIVES, THEIR PREPARATION AND THEIR USE AS MEDICINAL AGENTS

This is a division, of application Ser. No. 07/023,752 filed Mar. 9, 1987 now U.S. Pat. No. 4,877,792.

BACKGROUND OF THE INVENTION

This invention relates to novel heteroaryloxy-β-carboline derivatives, their preparation and their use as medicinal agents.

SUMMARY OF THE INVENTION

It is an object of the invention to provide new compounds having pharmacological properties.

Upon further study of the specification and appended claims, further objects and advantages of this invention will become apparent to those skilled in the art.

These objects have been achieved by providing heteroaryloxy-,β-carboline derivatives of Formula I

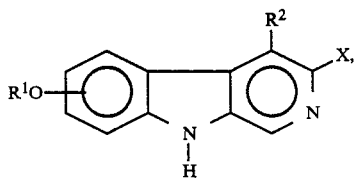

wherein $R^1$ is an optionally substituted heteroaryl residue, $R^2$ is hydrogen, lower alkyl or lower alkoxyalkyl, X is $COOR^3$, $—CONR^4R^5—$ or oxadiazolyl of the formula

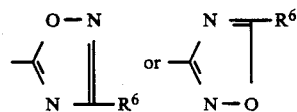

$R^3$ is H or lower alkyl, $R^4$ and $R^5$ independently are each H or alkyl, or $R^4$ and $R^5$ together form with the connecting nitrogen atom, a 5-6 membered heterocycle, and $R^6$ is hydrogen, lower alkyl or cycloalkyl.

The compounds of this invention possess valuable pharmacological properties. They influence, in particular, the central nervous system and thus are suitable as psychopharmaceuticals.

The substituent $OR^1$ can occur in the 5-, 6-, 7-, or 8-position preferably in the 5- or 6-position The heteroaromatic $R^1$ group is, for example, 5- or 6-membered and can optionally be mono- or polysubstituted, the substituent being located in any desired position of the heteroaromatic. Nitrogen-containing aromatics e.g., containing 1-2 N atoms are preferred as 6-membered ring heteroaromatics, for example, pyridine, pyrimidine, pyrazine and pyridazine, etc. Suitable 5-membered ring heteroaromatics include oxygen-, sulfurand/or nitrogen-containing aromatics, for example, furan, thiophene, pyrrole, imidazole, etc., e.g., generally containing 1-2 such atoms.

Examples of suitable substituents of the heteroaromatic rings include halogens, such as fluorine, chlorine or bromine, nitro, amino, nitrilo, lower alkyl and loweralkoxycarbonyl groups. Generally there are 1-3, preferably 1-2, substituents.

The point of attachment of the heteroaryl ring to the 0-atom in $OR^1$ can be preferably by any C-atom.

Suitable lower alkyl portions throughout include straight chained as well as branched, saturated residues of $C_1$-$C_6$ carbon atoms. Examples that can be cited are methyl, ethyl, n-propyl, isopropyl, n-butyl, isobutyl, tert-butyl, sec-butyl, a pentyl, a hexyl, etc. $C_1$-$C_4$ alkyl residues are preferred.

$C_{1-3}$-alkyls are preferred for the residues $R^4$ and $R^5$ If $R^4$ and $R^5$, together with the nitrogen atom, form a heterocycle, then the latter is typically saturated aliphatic and is 5- to 6-membered and can contain an additional hetero atom, such as sulfur, nitrogen or oxygen, e.g., morpholine, piperidine, thiomorpholine, piperazine, pyrrolidine, imidazolidine, pyrazolidine, or isothiazolidine, etc.

Suitable cycloalkyl residues $R_6$ can contain 3-7 carbon atoms, rings of 3-5 carbon atoms being preferred, for example, cyclopropyl, methylcyclopropyl, cyclobutyl, cyclopentyl, etc.

It is known that certain sites in the central nervous system of vertebrates exhibit high specific affinity for binding 1,4and 1,5-benzodiazepines (Squires, R.F. and Braestrup, C., Nature [London]266: 734 [1977]). These sites are called benzodiazepine receptors.

The receptor affinity, important for the pharmacological properties of the compounds according to the invention, was determined by investigating their capacity for displacing radioactively labeled flunitrazepam from benzodiazepine receptors.

The displacement activity of the compounds according to the invention is indicated as $IC_{50}$ and $ED_{50}$ which values. The $IC_{50}$ value indicated the concentration which effects a 50% displacement of the specific binding of $^3H$-flunitrazepam (1.0 nM, 0° C.) in samples with a total volume of 0.55 ml of a suspension of brain membranes, e.g., of rats.

The displacement test is performed as follows:

0 5 ml. of a suspension of untreated rat forebrains in 25 mM $KH_2PO_4$, pH=7.1 (5-10 mg tissue/sample) is incubated for 40-60 minutes at 0° C. together with $^3H$-diazepam (specific activity 14.4 Ci/mmol, 1.9 nM) or $^3H$-flunitrazepam (specific activity 87 Ci/mmol, 1.0 nM). After incubation, the suspension is filtered through a porous glass filter, the residue is washed twice with cold buffer solution, and radioactivity is measured in a scintillation counter.

The test is then repeated but so that before addition of the radioactively labeled benzodiazepine a specific amount or an excess amount of the compound, the displacement activity of which is to be determined, is added. Then the $IC_{50}$ value can be calculated on the basis of the values obtained.

The $ED_{50}$ value represents the dose of a test compound causing a reduction of specific binding of flunitrazepam to the benzodiazepine receptor in a live brain to 50% of the control value.

The in vivo test is performed as follows:

The test compound is injected into groups of mice in varying doses and normally intraperitoneally. After 15 minutes, $^3H$-flunitrazepam is administered to the mice intravenously. After another 20 minutes, the mice are sacrificed, their forebrain is removed, and the radioactivity specifically bound to the brain membranes is measured by scintillation counting. The $ED_{50}$ value is determined from the dose/effect curves.

The novel compounds of general Formula I exhibit valuable pharmacological properties. In particular, they act on the central nervous system and thus are suitable as psychopharmaceuticals in human medicine.

The compounds of this invention display especially anxiolytic and anticonvulsive activities. In order to study the anxiolytic effect, the compounds were tested in the 4-plate assay according to the method by Boissier et al., Eur. J. Pharmacol. 4 : 145-150 (1986). The table indicates the minimum lowest dose (MED) which increases the locomotor activity of the punished mice after i.p. treatment.

TABLE

| $R^1$ | $R^2$ | X | Inhibition of $^3$H-Flunitrazepam Binding | | Anxiolytic Activity |
|---|---|---|---|---|---|
| | | | $IC_{50}$ ng/ml in vitro | $ED_{50}$ mg/kg in vivo | MED mg/kg i.p. |
| 6-pyridyl-phenyl-Br | CH$_2$OCH$_3$ | COO-i-prop | 0.75 | 2.7 | 3.13 |
| 5-pyridyl-phenyl-pyridyl | H | oxadiazolyl-C$_2$H$_5$ | 0.28 | 2.8 | 3.13 |

The compounds of general Formula I can be utilized especially for the treatment of anxiety accompanied by depressions, epilepsy, sleep disturbances, spasticities, and muscle relaxation during anesthesia. The compounds according to the invention also show amnestic or memory-improving properties. As a result they are useful in treating Alzheimer's disease and memory loss (amnesia) after accidents. The latter properties are especially useful in geriatric patients.

The compounds of this invention can be used for the formulation of pharmaceutical preparations, for example for oral and parenteral use in accordance with conventional methods of galenic pharmacy.

Suitable auxiliary agents for formulating pharmaceutical preparations are those physiologically compatible, organic or inorganic excipients for enteral and parenteral use which are inert with respect to the compounds of this invention. Examples of excipients include: water, saline solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose, and polyvinylpyrrolidone. The pharmaceutical preparations can be sterilized and/or combined with auxiliary materials, such as lubricants, preservatives, stabilizers, wetting agents, emulsifiers, buffers, and colorants.

Especially suited for parenteral utilization are injection solutions or suspensions, particularly aqueous solutions of the active compounds in polyhydroxymethoxylated castor oil.

Particularly suited for oral administration are tablets, dragees or capsules with talc and/or hydrocarbon vehicles or binders, such as, for example, lactose, cornstarch or potato starch. Use can also take place in the liquid form, such as, for example, as an elixir to which optionally a sweetener has been added.

The compounds of this invention are usually administered in a dosage unit of 0.05-100 mg of active compound in a physiologically compatible excipient. The compounds according to - 5 the invention are usually administered in a dose of 0.1-300 mg/day, preferably 1-30 mg/day e.g., as anxiolytics, for example, analogous to the known agent diazepam.

The compounds of this invention can be prepared in accordance with methods known per se.

For example, the compounds of general Formula I can be prepared by processes wherein (a) an indole of general Formula II

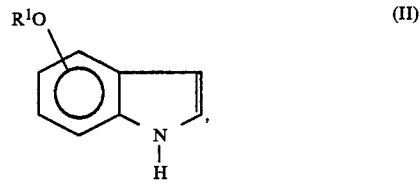

(II)

wherein $R^1$ has the meanings given in Formula I is reacted, in the presence of acids, with an azabutadiene of Formula III

(III)

Wherein X is COOR$^3$- group with $R^3$ meaning lower alkyl or an oxadiazolyl residue of the formula

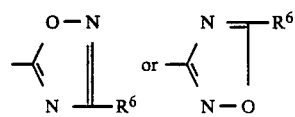

with $R^6$ having the above-indicated meanings; or
(b) a β-carboline derivative of general Formula IV

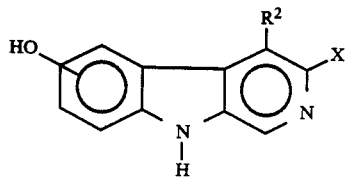

wherein X and R² have the meanings given above, is etherified with halogen-R¹, wherein R¹ has the meanings indicated above; or (c) a compound of Formula V

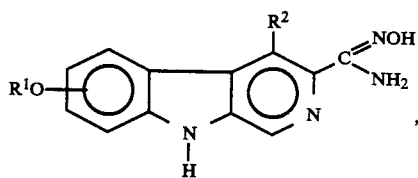

wherein R¹ and R² have the meanings given above, is reacted with a compound of the formula $(R^6CO)_2O$ wherein R⁶ has the meanings indicated above, to form a compound of general Formula I wherein X means

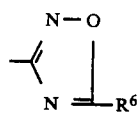

with R⁶ having the meanings given above and then optionally the compounds produced in accordance with process (a), (b) or (c), (α) wherein R¹ means O₂N-heteroaryl, are reduced to H₂N-heteroaryl compounds and these are, if desired, subsequently converted into N≡C-heteroaryl compounds, and (β) wherein R¹ means halogen heteroaryl, are dehalogenated, and (γ) wherein X means COOR³ with R³ being lower alkyl, are interesterified or saponified, and the thusobtained compounds wherein R³ means hydrogen are optionally amidated to compounds wherein X means CONR⁴R⁵ with R⁴ and R⁵ having the meanings given above, or are reacted, with an amidoxime of the formula R⁶—CNH (=NOH) wherein R⁶ has the above-indicated meanings, to compounds wherein X means

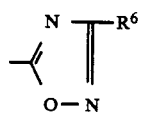

with R⁶ having the meanings given above.

In accordance with process (a), reaction of the indole derivative of general Formula II with the azadiene takes place in the presence of acids at temperatures of between 50° and 200° C The reaction is performed, for example, by heating the indole derivative and the azabutadiene of Formula III in an aliphatic carboxylic acid, such as formic acid, acetic acid, propionic acid or trifluoroacetic acid, or in an inorganic medium, such as phosphoric acid, polyphosphoric acid, etc. It is also possible to add inert organic solvents, such as, for example, toluene, ethyl acetate, dioxane, dimethoxyethane, acetonitrile, dichloromethane, etc.

However, the reaction can also be conducted in the presence of catalytic amounts of a mineral acid, such as sulfuric acid, hydrochloric acid, perchloric acid, etc., in one of the previously recited, inert solvents, and is generally completed after 2-10 hours.

Etherification of the β-carboline derivatives of general Formula IV in accordance with process (b) takes place, for example, by reacting a reactive heteroaryl compound in a polar solvent, e.g. dimethyl sulfoxide, dimethylformamide, acetonitrile or ethanol, in the presence of a base at temperatures up to the boiling point of the solvent. Especially suitable as the reactive heteroaryl compounds are the halogenides, such as chloride, bromide, or iodide, as well as mesylate or tosylate.

The bases employed can be alkali compounds, such as, for example, sodium or potassium hydroxide, sodium or potassium carbonate, and others, optionally also in the presence of phase transfer catalysts, e.g. crown ethers or "Aliquat" 336. The process is advantageously performed under inert gas atmosphere, for example under nitrogen or argon.

Reduction of the nitro group to the amino group can be effected, for example, catalytically in polar solvents, at room temperature under H₂ pressure or under normal pressure. Preferably, palladium on a support, such as carbon or platinum, in finely divided form, is utilized as the catalyst. Suitable polar solvents for the reduction are: for example, alcohols or ethers, such as methanol, ethanol, diethyl ether, tetrahydrofuran, or their mixtures, etc.

Introduction of the cyano group takes place, for example, in accordance with the Sandmeyer reaction by reacting the diazonium salts, formed intermediately from the amino compounds with nitrites, in the presence of Cu(I) cyanide with alkali cyanides.

Catalytic dehalogenation is performed, for example, with palladium on carbon (10%) with the addition of organic bases, such as, for example, triethylamine in alcohol. In order to avoid interesterifications, the alcohol of the ester component is suitably employed as the solvent. If interesterification is desired, then it is possible, for example, to carry out the reaction with the corresponding alcohol or alkali alcoholate; if desired, titanium tetraisopropylate can be added as the catalyst in the anhydrous alcohol. Customarily, the interesterification is performed at temperatures of 60-120° C. and is ended after 2-6 hours.

Introduction of the tert-butyl ester group takes place, for example, by reacting the carboxylic acid with tert-butoxybisdimethylaminomethane. In general, the reaction is conducted under an inert gas atmosphere, such as argon or nitrogen and under exclusion of moisture at an elevated temperature.

Saponification of the ester group can take place in an acidic or alkaline process; preferably, an alkaline saponification is carried out by heating the ester with dilute aqueous alkali solution, such as potassium or sodium hydroxide, in a protic solvent, such as, for example, methanol, ethanol or ethylene glycol, to temperatures up to the reflux temperature of the reaction mixture.

Carboxylic acid amides are obtained, for example, by reaction with amines from the corresponding imidazolides, which latter are produced intermediately from the carboxylic acids and carbonyl- or thionyldiimidazole. The reaction is performed at room temperature in dipolar aprotic solvents, such as, for example, dimethylformamide, dimethylacetamide, etc.

For the introduction of the 1,2,4-oxadiazol-5-yl residue, the β-carboline-carboxylic acid is made to condense, for example, with an amidoxime of the formula $$R^2-C(=NOH)NH_2$$

in an inert solvent boiling above 100° C and inert with respect to the reactants, at the reflux temperature of the reaction mixture. Suitable solvents for the condensation reaction are, for example, toluene and dimethylformamide. Advantageously, the free β-carboline-3-carboxylic acid is suitably activated prior to the condensation reaction. For this purpose, the free acid can be converted, for instance, into the mixed anhydride, into the activated ester, or into the chloride. Also advantageous proved to be activation to the imidazolide with imidazole/thionyl chloride or also carbonyldiimidazole in an aprotic solvent, such as dioxane, tetrahydrofuran, dimethylformamide or N-methylpyrrolidone, at temperatures of between 0° C. and 50° C., preferably at room temperature.

The 1,2,4-oxidiazol-3-yl-,β-carboline derivatives are produced, for example, from the ,β-carboline-3-carboxylic acids by converting the acid amides, prepared as usual, with agents splitting off water, e.g., a reagent from triphenylphosphine/bromine in the presence of triethylamine, into the corresponding nitriles. These can subsequently be reacted with hydroxylamine to the desired β-carboline-3carboxamidoximes The resultant β-carboline-3-carboxamidoximes are combined at room temperature with the acid anhydride ($R^6CO)_2O$ and then heated to the boiling temperature. The reaction is finished after 7 hours and working up is conducted according to the usual methods.

The starting materials required are all known or readily preparable from known starting materials using fully conventional methods. See, for example, EP-A-54507 and EP-A-110813.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperature are set forth uncorrected in degrees Celsius and all parts and percentages are by weight; unless otherwise indicated.

Example 1

5-(2-Pyrazinyloxy)-β-carboline-3-carboxylic Acid Ethyl Ester

Under ice cooling, a mixture of 2 ml of glacial acetic acid and 0.3 ml of trifluoroacetic acid is combined with 260 mg of 1,4-bis(dimethylamino)-2-azabutadiene-3-carboxylic acid ethyl ester and stirred for 10 minutes. Then 211 mg of 4-(2-pyrazinyloxy)indole is added and the mixture agitated under a nitrogen atmosphere at room temperature for 24 hours and subsequently heated for 2 hours under reflux (150-160° C. bath temperature). After cooling, the mixture is poured into $K_2CO_3$ solution, the crystallized product is suctioned off, rinsed with water, and recrystallized from ethanol, thus obtaining 190 mg (56%), mp 264-266° C. (EtOH).

The starting material is obtained as follows:

A solution of 2.66 g of 4-hydroxyindole in 60 ml of DMSO is combined with 1.4 g of potassium hydroxide (pulverized) and stirred under an $N_2$ atmosphere for one hour at room temperature. After adding 2.5 g of 2-chloropyrazine, the mixture is heated for 2 hours to 100° C., poured into water, and extracted with ethyl acetate. The residue from the organic phase is purified over silica gel, thus obtaining 2.95 g (70%) of 4-(2-pyrazinyloxy)indole, mp 192-193° C.

Example 2

5-(5-Nitro-2-pyridyloxy)-β-carboline-3 carboxylic Acid Ethyl Ester

Melting point 298-300° C. Analogously to Example 1 from 4-(5-nitro-2-pyridyloxy)indole.

The starting material is obtained analogously to Example 1 from 4-hydroxyindole and 2-chloro-5nitropyridine, mp 169-170° C.

Example 3

5-(2-Pyrimidinyloxy)-β-carboline-3-carboxylic Acid Ethyl Ester

Melting point 273-275° C. Analogously to Example 1 from 4-(2-pyrimidinyloxy)indole.

The starting material is produced analogously to Example 1 from 4-hdyroxyindole and 2-chloropyrimidine, mp 233-234° C. (diisopropyl ether).

Example 4

3-(3-Ethyl-1,2,4-oxadiazol-5-yl)-5-(2-pyrazinyloxy)-β-carboline

Under ice cooling, a mixture of 4 ml of glacial acetic acid and 0.5 ml of trifluoroacetic acid is combined with 340 mg of 1,4-bis(dimethylamino)-3 3-ethyl-1,2,4-oxadiazolyl-5-yl)-2-azabutadiene and stirred for 10 minutes. Thereafter, 211 mg of 4(2-pyrazinyloxy)indole is added, and the mixture is maintained first at room temperature for 24 hours, then 2 hours at 100° C., and finally for 6 hours under reflux. After processing with $K_2CO_3$ solution, the product is chromatographed over silica gel, thus obtaining 92 mg (25%), mp 278-280° C. (EtOH).

The azadiene is obtained as follows:

(A) 3-Ethyl-5-(phthalimidomethyl)-1,2,4-oxadiazole

At 40° C., a suspension of 26.0 g of carbonyldiimidazole in 250 ml of THF is added to a solution of 65.7 g of phthalimidoacetic acid in 500 ml of THF (absolute). After about one hour, no release of gas can be observed any longer. At this point in time, a solution of 28.2 g of propionamidoxime in 50 ml of THF— is added, and the mixture is stirred at room temperature for 24 hours. After the precipitate has been filtered off, the filtrate is concentrated under vacuum and, after addition of 500 ml of dry xylene, is heated under reflux for 6 hours on a water trap. The still hot solution is separated from the oily residue and concentrated under vacuum. Crystallization from EtOH yields 31.5 g (76.5%, based on carbonyldiimidazole) of oxadiazole having a melting point of 106-107° C.

(B) 5-Aminomethyl-3-ethyl-1,2,4-oxadiazole

A suspension of 32.2 g of phthalimide in 250 ml of methanol is combined at room temperature with 4.5 g (140 mmol) of hydrazine, the compound being quickly dissolved. The reaction mixture is refluxed for 3 hours, then the resultant precipitate is suctioned off, rinsed with methanol, and the filtrate is concentrated. After making the residue into a slurry with diethyl ether, the mixture is again filtered, concentrated, and the oil distilled on a bulb tube, boiling point 90-100° C., 0.03 torr. Yield: 14.87 g (91.6% of theory); $n_D^{20} = 1.4691$.

(C) A mixture of 11.5 g of 5-aminomethyl-3-ethyl-1,2,4-oxadiazole and 24 ml of dimethylformamide dimethylacetal is heated to 80° C for 7 hours; during this process, 10 ml of thus-formed methanol is removed by distillation. After adding another 12 ml of DMF-acetal, the mixture is refluxed for 3 hours, then subjected to fractional distillation. The fraction passing over at 155-160° C and 0.03 torr, 1,4-bis(di-methylamino)-3-(3-ethyl-1,2,4-oxadiazol-1,3-butadiene is obtained in a yield of 72% of theory; $n_D^{20}=1.5908$.

Example 5

5-(5-Chloro-2-pyridyloxy)-3-(3-ethyl-1,2,4-oxadiazol-5-yl)-β-carboline

Analogously to Example 4 from 4-(5-chloro-2-pyridyloxy)indole,

Example 6

5-(2-Pyrimidinyloxy)-3-(3-ethyl-1,2,4-oxadiazol-5-yl)-β-carboline

In analogy to Example 4 from 4-(2-pyrimidinyloxy)indole, mp 254–256° C, (EtOH).

Example 7

5-(5-Nitro-2-pyridyloxy)-3-(3-ethyl-1,2,4-oxadiazol-5-yl)-β-carboline

Analogously to Example 4 from 4-(5-nitro-2-pyridyloxy)indole.

Example 8

4-Methoxymethyl-5-(2-pyrazinyloxy)-β-carboline-3-carboxylic Acid Ethyl Ester

A solution of 300 mg of 5-hydroxy-4-methoxy-methyl-β-carboline-3-carboxylic acid ethyl ester in 3 ml of dry dimethyl sulfoxide is combined with 155 mg of $K_2CO_3$ and stirred under nitrogen at room temperature for 30 minutes. After adding 0.2 ml of 2-chloropyrazine, the mixture is agitated for 6 hours at 95° C., then poured into 1N acetic acid and extracted with ethyl acetate. Purification over silica gel yields 242 mg (64%), mp 130–131° C. (diethyl ether). The starting material is obtained by catalytic hydrogenation (Pd/C/H2 in EtOH) of the 5-benzyloxy-4methoxymethyl-β-carboline-3-carboxylic acid ethyl ester.

Example 9

4-Methoxymethyl-5-(2-pyrimidinyloxy)-β-carboline-3-carboxylic Acid Ethyl Ester

Analogously to Example 8 from 2-chloropyrimidine in acetonitrile, mp 96–98° C. (EtOH).

Example 10

5-(5-Chloro-2-pyridyloxy)-4-methoxymethyl-β-carboline-3-carboxylic Acid Ethyl Ester In analogy to Example 8 from 2-bromo-5-chloropyridine in dimethylformamide, mp 156–158° C. (diisopropyl ether).

Example 11

5-(5-Chloro-2-pyridyloxy)-4-methyl-β-carboline-3-carboxylic Acid Ethyl Ester

Analogously to Example 8 from 5-hydroxy-4-methyl-β-carboline-2-carboxylic acid ethyl ester and 2-bromo-5-chloropyridine in dimethylformamide, mp 194–196° C. (EtOH).

Example 12

6-(5-Nitro-2-pyridyloxy)-β-carboline-3-carboxylic Acid Methyl Ester

In analogy to Example 8 from 6-hydroxy-β-carboline-3-carboxylic acid methyl ester and 2-chloro-5-nitropyridine, mp 150–155° C.

Example 13

4-Methoxymethyl-6-(2-pyrimidinyloxy)-β-carboline-3-carboxylic Acid Ethyl Ester

Analogously to Example 8 from 6-hydroxy-4-methoxymethyl-β-carboline-3-carboxylic acid ethyl ester and 2-chloropyrimidine, mp 128–129° C.

Example 14

6-(5-Bromo-2-pyridyloxy)-4-methoxymethyl-β-carboline-3-carboxylic Acid Ethyl Ester In analogy to Example 8 from 6-hydroxy-4-methoxymethyl-β-carboline-3-carboxylic acid ethyl ester with 2,5-dibromopyridine, mp 210–212° C.

Example 15

5-(2-Pyrimidinyloxy)-8-carboline-3-carboxylic Acid Isopropyl Ester

A suspension of 185 mg of 5-(2-pyrimidinyloxy)-β-carboline-3-carboxylic acid ethyl ester in 20 ml of absolute 2-propanol is combined with 0.16 ml of titanium isopropylate and refluxed for 90 minutes under an argon atmosphere. After concentration and purification over silica gel, 124 mg (64%) of isopropyl ester is obtained, mp 298–300° C. (isopropanol).

Example 16

5-(5-Chloro-2-pyridyloxy)-4-methoxymethyl-β-carboline-3-carboxylic Acid Isopropyl Ester Analogously to Example 15 from the corresponding ethyl ester, mp 190–191° C. (isopropanol).

Example 17

5-(5-Chloro-2pyridyloxy)-4-methyl-β-carboline-3-carboxylic Acid Isoproyl Ester

Analogously to Example 15 from the corresponding ethyl ester, mp 243–245° C. (isopropanol).

Example 18

6-(5-Bromo-2-pyridyloxy)-4-methoxymethyl-β-carboline-3-carboxylic Acid Isopropyl Ester In analogy to Example 15 from the corresponding ethyl ester, mp 210–212° C.

Example 19

4-Methoxymethyl-6-(2-pyrimidinyloxy)-β-carboline-3-carboxylic Acid Isopropyl Ester Analogously to Example 15 from the corresponding ethyl ester, mp 166–169° C.

Example 20

5-(2-Pyrazinyloxy)-4-methoxymethyl-β-carboline-3-carboxylic Acid

A suspension of 235 mg of 4-methoxymethyl-5-(2-pyrazinyloxy)-β-carboline-3-carboxylic acid ethyl in 2.5 ml of 1N sodium hydroxide solution is heated to 110° C. for 30 minutes After cooling, the mixture is adjusted to pH 3 with 2N HCl, the crystallized product is suctioned off and rinsed, yielding 265 mg (88%), mp 236–237° C.

Analogously there are obtained 4-methoxymethyl-5-(2-pyrimidinyloxy)-β-carboline-3carboxylic acid, mp 237–239° C., 5-(5-chloro-2-pyridyloxy)-4-methoxymethyl-β-carboline-3-carboxylic acid, mp 226–227° C.

Example 21

3-(3-Ethyl-1,2,4-oxadiazol-5-yl)-4-methoxymethyl-5-(2-pyrazinyloxy)-β-carboline

A solution of 245 mg of 4-methoxymethyl-52-pyrazinyloxy)-β-carboline-3-carboxylic acid in 15 ml of dimethylformamide is combined with 140 mg of N,N'-carbonyldiimidazole and stirred for one hour at 50° C. Then 310 mg of propionamidoxime is added and the mixture is stirred for 8 hours at room temperature, then another 2 hours at 100° C. After concentration under vacuum, the residue is combined with 20 ml of xylene and refluxed for 3 hours. The filtered xylene phase is concentrated and the residue purified over silica gel, thus obtaining 170 mg (60%), mp 192–193° C. (ethanol).

Analogously there are obtained 3-(3-ethyl-1,2,4-oxadiazol-5-yl)-4-methoxymethyl-5-2-pyrimidinyloxy)-β-carboline, mp 175–176° C. (EtOH), 5-(5-chloro-2-pyridyloxy)-4-methoxymethyl-3-(3-ethyl-1,2,4-oxadiazol-5-yl)-β-carboline, mp 144–146° C. (diisopropyl ether).

Example 22

5-(5-Chloro-2-pyridyloxy)-4-methoxymethyl-β-carboline-3-carboxylic Acid Isopropylamide From the 3-carboxylic acid imidazolide and isopropylamine.

Example 23

4-Methoxymethyl-5-(2-pyridyloxy)-β-carboline-3-carboxylic Acid Isopropyl Ester

A suspension of 124 mg of 5-(5-chloro-2-pyridyloxy)-4-methoxymethyl-β-carboline-3-carboxylic acid isopropyl ester in 15 ml of 2-propanol is combined with 50 mg of triethylamine and 120 mg of Pd-C (10%) and hydrogenated at room temperature and under normal pressure. After absorption of the stoichiometric quantity of hydrogen the mixture is filtered, the filtrate is concentrated, and the residue is recrystallized from 2-propanol, thus obtaining 96 mg (84%), mp 188–189° C.

Example 24

6-(5-Amino-2-pyridyloxy)-β-carboline-3-carboxylic Acid Methyl Ester

A suspension of 3.65 g of 6-(5-nitro-2-pyridyloxy)-β-carboline-3-carboxylic acid methyl ester and 0.5 g of Pd-C (10%) in 100 ml of methanol is hydrogenated at room temperature and under normal pressure. After absorption of the stoichiometric amount of hydrogen, the mixture is filtered and concentrated. The residue is crystallized from methanol/diethyl ether, yielding 2.84 g (85%).

Example 25

6-(5-Cyano-2-pyridyloxy)-β-carboline-3-carboxylic Acid Methyl Ester

A suspension of 1.7 g of amino derivative (Example 24) in 10 ml of water and 2.5 ml of hydrochloric acid (37%) is combined dropwise at -5° C. with a solution of 0.4 g of NaNO₂ in 1.5 ml of water, then stirred for another hour at 0–5° C. By adding sodium carbonate, the solution is then adjusted to pH 5.5–6 and poured into a mixture, preheated to about 60° C., of 0.5 g of copper (I) cyanide and 1.6 g of potassium cyanide in 10 ml of water. After the reaction is completed, the cooled-off solution is extracted with dichloromethane, the organic phase is washed with water and concentrated. The residue is purified over silica gel, thus obtaining 1.12 g (65%).

Example 26

4-Methoxymethyl-5-(5-nitro-2-thiazolyloxy)-β-carboline-3-carboxylic Acid Ethyl Ester Analogously to Example 8 from 2-bromo-5nitrothiazole.

Example 27

5-(5-Ethoxycarbonyl-2-furyloxy)-4-methoxy-methyl-β-carboline-3-carboxylic Acid Ethyl Ester Analogously to Example 8 from 5-bromofuran-2carboxylic acid ethyl ester.

Example 28

5-(5-Formyl-2-thienyloxy)-4-methoxymethyl-β-carboline-3-carboxylic Acid Ethyl Ester In analogy to Example 8 from 5-bromothiophene-2-carbaldehyde.

Example 29

4-Methoxymethyl-5-(5-nitro-2-thiazolyloxy)-β-carboline-3-carboxylic Acid Isopropyl Ester Produced analogously to Example 8 from 5-hydroxy-4-methoxymethyl-βcarboline-3-carboxylic acid ethyl ester and 2-bromo-5-nitrothiazole and subsequent ester interchange analogously to Example 15. mp 190–192° C. (isopropanol)

Example 30

5-(5-Ethoxycarbonyl-2-furyloxy)-4-methoxymethyl-β-carboline-3-carboxylic Acid Isopropyl Ester Prepared analogously to Example 29 from 5-bromofuran-2-carboxylic acid ethyl ester; mp 191–192° C. (isopropanol).

Example 31

4-Methoxymethyl-5-(2-thiazolyloxy)-β-carboline-3-carboxylic Acid Isopropyl Ester Produced in analogy to Example 29 from 2-bromothiazole; mp 123–125° C. (ethyl acetate).

Example 32

6-(5-Bromo-2-pyridyloxy)-4-methoxymethyl-β-carboline-3-carboxylic Acid tert-Butyl Ester Produced from the corresponding acid by heating with tert-butoxybis(dimethylamino)methane, mp 173–175° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing form the spirit and scope thereof, can make various changes and modifications of the invention to adapt it to various usages and conditions.

What is claimed is:

1. A heteroaryloxy-β-carboline of the formula

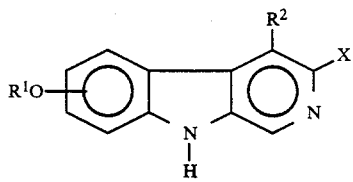

wherein
$R^1$ is pyrimidine, pyrazine or pyridazine or such a group substituted by halo, nitro, amino, cyano, $C_{1-6}$-alkyl, or $(C_{1-6}$-alkoxy)carbonyl,
$R^2$ is hydrogen, $C_{1-6}$-alkyl or $C_{1-6}$ alkoxy-$C_{1-6}$-alkyl,
X is $COOR^3$, $CONR^4R^5$, or oxadiazoyl of the formula

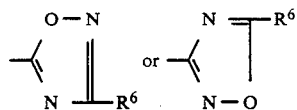

$R^3$ is H or $C_{1-6}$-alkyl,
$R^4$ and $R^5$ independently are each H or $C_{1-6}$-alkyl, or $R^4$ and $R^5$ together form with the connecting nitrogen atom, an aliphatic, saturated 5- or 6-membered heterocycle, or a 5-or 6-membered heterocycle containing an O, S or second N atom, and
$R^6$ is hydrogen, $C_{1-6}$-alkyl or $C_{3-7}$-cycloalkyl.

2. A compound of claim 1 wherein $R^2$ is alkyl or alkoxyalkyl.

3. A compound of claim 1 wherein $R^1O$ is in the 5- or 6- position.

4. A compound of claim 1 wherein $R^1$ is attached to O by a C-atom.

5. A compound of claim 1 wherein $R^4$ and $R^5$ are $C_{1-3}$-alkyl.

6. A compound of claim 1 wherein $R^4$ and $R^5$ together form morpholine, piperidine, thiomorpholine, piperazine, pyrrolidine, imidazolidine, pyrazolidine, or isothiazolidine.

7. A compound of claim 1 wherein $R^6$ is cycloalkyl.

8. A compound of claim 1 wherein $R^6$ is H or alkyl.

9. A compound of claim 1 wherein X is $COOR^3$.

10. A compound of claim 1 wherein X is $CONR^4R^5$.

11. A compound of claim 1 wherein X is oxadiazolyl.

12. 5-(2-Pyrazinyloxy)-β-carboline-3-carboxylic acid ethyl ester,
5-(2pyrimidinyloxy)-β-carboline-3-carboxylic acid ethyl ester,
3-(3-ethyl-1,2,4-oxadiazol-5-yl)-5(2-pyrazinyloxy)-β-carboline,
5-(2-pyrimidinyloxy)-3-(3-ethyl-1,2,4-oxadiazol-5-yl)-β-carboline,
4-methoxymethyl5-(2-pyrazinyloxy)-β-carboline-62-carboxylic acid ethyl ester,
4-methoxymethyl-5-(2-pyrimidinyloxy)-β-carboline-3-carboxylic acid ethyl ester,
4-methoxymethyl-6-(2-pyrimidinyloxy)-β-carboline-3-carboxylic acid ethyl ester,
5-(2-pyrimidinyloxy)-β-carboline-3-carboxylic acid isopropyl ester,
4-methoxymethyl-6-(2-pyrimidinyloxy)-β-carboline-3-carboxylic acid isopropyl ester,
5-(2-pyrazinyloxy)-4-methoxymethyl-β-carboline-3-carboxylic acid,
4-methoxymethyl-5-(2-pyrimidinyloxy)-β-carboline-3-carboxylic acid,
3-(3-ethyl-1,2,4-oxadiazol-5-yl)-4-methoxymethyl-5-(2-pyrazinyloxy)-β-carboline,
or 3-(3-ethyl-1,2,4-oxadiazol-5-yl)-4-methoxymethyl-5-(2-pyrimidinyloxy)-β-carboline.

13. A pharmaceutical composition comprising an effective amount of a compound of claim 1 and a pharmaceutically acceptable carrier.

14. A composition comprising 0.05–100 mg of a compound of claim 1 and a pharmaceutically acceptable carrier.

15. A method of achieving an anxiolytic effect comprising administering a compound of claim 1.

16. A method of achieving an anticonvulsant effect comprising administering a compound of claim 1.

17. A method of claim 15 for treating anxiety accompanied by depression, epilepsy, sleep disturbance or spasticity of for achieving muscle relaxation during anesthesia.

* * * * *

UNITED STATES PATENT AND TRADEMARK OFFICE
CERTIFICATE OF CORRECTION

PATENT NO. : 4,960,777
DATED : October 2, 1990
INVENTOR(S) : Helmut Biere et al

It is certified that error appears in the above-identified patent and that said Letters Patent is hereby corrected as shown below:

Column 14, Claim 12, line 16:

Reads: "4-methoxymethyl 5-(2-pyrazinyloxy)-$\beta$-carboline-62"

Should Read: --4-methoxymethyl-5-(2-pyrazinyloxy)-$\beta$-carboline-3--

Signed and Sealed this

Fourth Day of February, 1992

Attest:

HARRY F. MANBECK, JR.

Attesting Officer

Commissioner of Patents and Trademarks